(12) United States Patent
Jung

(10) Patent No.: US 11,754,438 B2
(45) Date of Patent: Sep. 12, 2023

(54) SELF-CHECKING PHOTOELECTRIC SENSOR AND METHOD OF OPERATION

(71) Applicant: Alcon Inc., Fribourg (CH)

(72) Inventor: Christopher Carl Jung, Mission Viejo, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/651,308

(22) Filed: Feb. 16, 2022

(65) Prior Publication Data

US 2022/0268625 A1 Aug. 25, 2022

Related U.S. Application Data

(60) Provisional application No. 63/152,427, filed on Feb. 23, 2021.

(51) Int. Cl.
| | |
|---|---|
| *G01J 1/02* | (2006.01) |
| *A61F 9/007* | (2006.01) |
| *G01J 1/08* | (2006.01) |
| *G01N 21/94* | (2006.01) |
| *G01N 21/15* | (2006.01) |

(52) U.S. Cl.
CPC ........ *G01J 1/0228* (2013.01); *A61F 9/00736* (2013.01); *G01J 2001/083* (2013.01); *G01N 21/15* (2013.01); *G01N 21/94* (2013.01); *G01N 2021/157* (2013.01); *G01N 2021/945* (2013.01); *G01N 2201/062* (2013.01)

(58) Field of Classification Search
CPC .............. G01J 1/0228; G01J 2001/083; A61F 9/00736; A61F 9/008; A61F 2009/00872; G01N 21/94; G01N 21/53; G01N 21/15; G01N 2021/157; G01N 2021/945; G01N 2201/062; G01N 21/85; G01N 21/49; G01N 21/3577

See application file for complete search history.

(56) References Cited

U.S. PATENT DOCUMENTS

| | | | | |
|---|---|---|---|---|
| 6,806,947 | B1* | 10/2004 | Ekdahl | ................ A61M 1/3626 |
| | | | | 356/614 |
| 2016/0099695 | A1* | 4/2016 | Kiritani | ............... H03F 3/45475 |
| | | | | 330/251 |
| 2018/0280616 | A1 | 10/2018 | Witt et al. | |
| 2019/0383963 | A1* | 12/2019 | Hayashi | ............. G01N 15/1434 |

(Continued)

*Primary Examiner* — Jennifer D Bennett
*Assistant Examiner* — Erin R Garber

(57) ABSTRACT

Certain embodiments provide a self-checking photoelectric sensor that is configured to determine a characteristic (e.g., an amount of blockage and/or wellness/decay) of an optical pathway (e.g., an electro-optical pathway). An example method generally includes increasing, over a time period that starts at a first time, a current input to a light emitting element (LEE). The method generally includes receiving, by a light detection element, an output of the LEE via the optical pathway during the time period. The method generally includes converting, during the time period, the LEE output to a voltage output. The method generally includes determining a second time in the time period when the voltage output crosses a threshold. The method generally includes determining the characteristic of the optical pathway between the LEE and the light detection element based on a difference between the second time and the first time.

7 Claims, 14 Drawing Sheets

(56) References Cited

U.S. PATENT DOCUMENTS

2020/0096405 A1\* 3/2020 Wan .......................... G01L 1/26
2020/0393365 A1\* 12/2020 Pierson ............... H03F 3/45475
2021/0136902 A1\* 5/2021 Chang ................... H05G 2/006
2022/0040718 A1\* 2/2022 Raynor ................ B05B 12/004

\* cited by examiner

US 11,754,438 B2

SELF-CHECKING PHOTOELECTRIC SENSOR AND METHOD OF OPERATION

PRIORITY CLAIM

This application claims the benefit of priority of U.S. Provisional Patent Application Ser. No. 63/152,427 titled "SELF-CHECKING PHOTOELECTRIC SENSOR AND METHOD OF OPERATION," filed on Feb. 23, 2021, whose inventor is Christopher Carl Jung, which is hereby incorporated by reference in its entirety as though fully and completely set forth herein.

TECHNICAL FIELD

The present disclosure relates generally to a self-checking photoelectric sensor that is configured to determine a characteristic (e.g., an amount of blockage, wellness/decay as a function of age, etc.) of an optical pathway (e.g., an electro-optical pathway).

BACKGROUND

Photoelectric sensors may be used to ascertain presence (or absence) of an object by using a light transmitter (e.g., emitting infrared light or visible light, such as a light emitting diode (LED)) and a photoelectric receiver. Photoelectric sensors can be implemented in a variety of situations for determining presence/absence of an obstruction. For example, photoelectric sensors may be implemented in a path (e.g., a fluid path) to determine whether the path is blocked or obstructed.

In one example, photoelectric sensors may be implemented in the fluid path of a vitreo-retinal procedure unit to help monitor the quality of the fluid path during a procedure. That is, fluid caught in the path, aspirated tissue, or any other form of blockage could be advantageously detected. Moreover, photoelectric sensors implemented in such a system can also be used to indicate the overall health/cleanliness of the light transmitter and/or receiver to warn of any degradation to the sensor system itself.

Vitreo-retinal procedures may include a variety of surgical procedures performed to restore, preserve, and enhance vision. Vitreo-retinal procedures may be appropriate to treat many serious conditions of the back of the eye. Vitreo-retinal procedures may treat conditions such as age-related macular degeneration (AMD), diabetic retinopathy and diabetic vitreous hemorrhage, macular hole, retinal detachment, epiretinal membrane, cytomegalovirus (CMV) retinitis, and many other ophthalmic conditions. For vitreo-retinal procedures, a handheld unit plugs into a port on a base unit where a fluid path can be monitored, for example, during operation.

BRIEF SUMMARY

The present disclosure relates generally to a self-checking photoelectric sensor that is configured to determine a characteristic of an optical pathway.

Certain embodiments provide a method for determining a characteristic of an optical pathway. The method generally includes increasing, over a time period that starts at a first time, a current input to a light emitting element (LEE). The method generally includes receiving, by a light detection element, an output of the LEE via the optical pathway during the time period. The method generally includes converting, during the time period, the LEE output to a voltage output. The method generally includes determining a second time in the time period when the voltage output crosses a threshold. The method generally includes determining the characteristic of the optical pathway between the LEE and the light detection element based on a difference between the second time and the first time.

Certain embodiments provide a method for determining a characteristic of an optical pathway. The method generally includes emitting a light output from an LEE over a time period that starts at a first time. The method generally includes receiving, by a light detection element via the optical pathway, the LEE output during the time period. The method generally includes converting, during the time period, the LEE output to a voltage output. The method generally includes varying a gain of an amplifier coupled to the voltage output during the time period to vary the voltage output. The method generally includes determining a second time in the time period when the voltage output crosses a threshold. The method generally includes determining the characteristic of the optical pathway between the LEE and the light detection element based on a difference between the second time and the first time.

Certain embodiments provide a method for determining a characteristic of an optical pathway. The method generally includes applying a first current input to an LEE. The method generally includes receiving, by a light detection element, an output of the LEE via the optical pathway while the first current input is applied to the LEE. The method generally includes converting the LEE output to a voltage output. The method generally includes determining whether the voltage output is greater than a first threshold. The method generally includes, when the voltage output is greater than the first threshold, applying a second current input to the LEE. The method generally includes, when the voltage output is greater than the first threshold, receiving, by the light detection element, the output of the LEE via the optical pathway while the second current input is applied to the LEE. The method generally includes, when the voltage output is greater than the first threshold, converting the LEE output to another voltage output. The method generally includes, when the voltage output is greater than the first threshold, determining whether the other voltage output is greater than a second threshold, where the second current is less than first current, and the second threshold is less than the first threshold. The method generally includes, when the voltage output is greater than the first threshold, determining the characteristic of the optical pathway based on whether the other voltage output is greater than the second threshold.

Certain embodiments provide a method for determining a characteristic of an optical pathway. The method generally includes applying a current input to an LEE. The method generally includes receiving, by a light detection element, an output of the LEE via the optical pathway while the current input is applied to the LEE. The method generally includes converting the LEE output to a voltage output while an amplifier coupled to the LEE is configured with a first gain. The method generally includes determining whether the voltage output is greater than a first threshold. The method generally includes, when the voltage output is greater than the first threshold, applying the current input to the LEE while the amplifier is configured with a second gain. The method generally includes, when the voltage output is greater than the first threshold, receiving, by the light detection element, the output of the LEE via the optical pathway while the current input is applied to the LEE and while the amplifier is configured with the second gain. The method generally includes, when the voltage output is greater than the first threshold, converting the LEE output to another voltage output. The method generally includes, when the voltage output is greater than the first threshold, determining whether the other voltage output is greater than a second threshold, where the second gain is less than first gain, and the second threshold is less than the first threshold. The method generally includes, when the voltage output is greater than the first threshold, determining the characteristic of the optical pathway based on whether the other voltage output is greater than the second threshold.

Aspects of the present disclosure provide means for, apparatus, processors, and computer-readable mediums for performing techniques and methods described herein.

The following description and the related drawings set forth in detail certain illustrative features of one or more embodiments.

BRIEF DESCRIPTION OF THE DRAWINGS

The appended drawings depict only examples of certain embodiments of the present disclosure and are therefore not to be considered as limiting the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
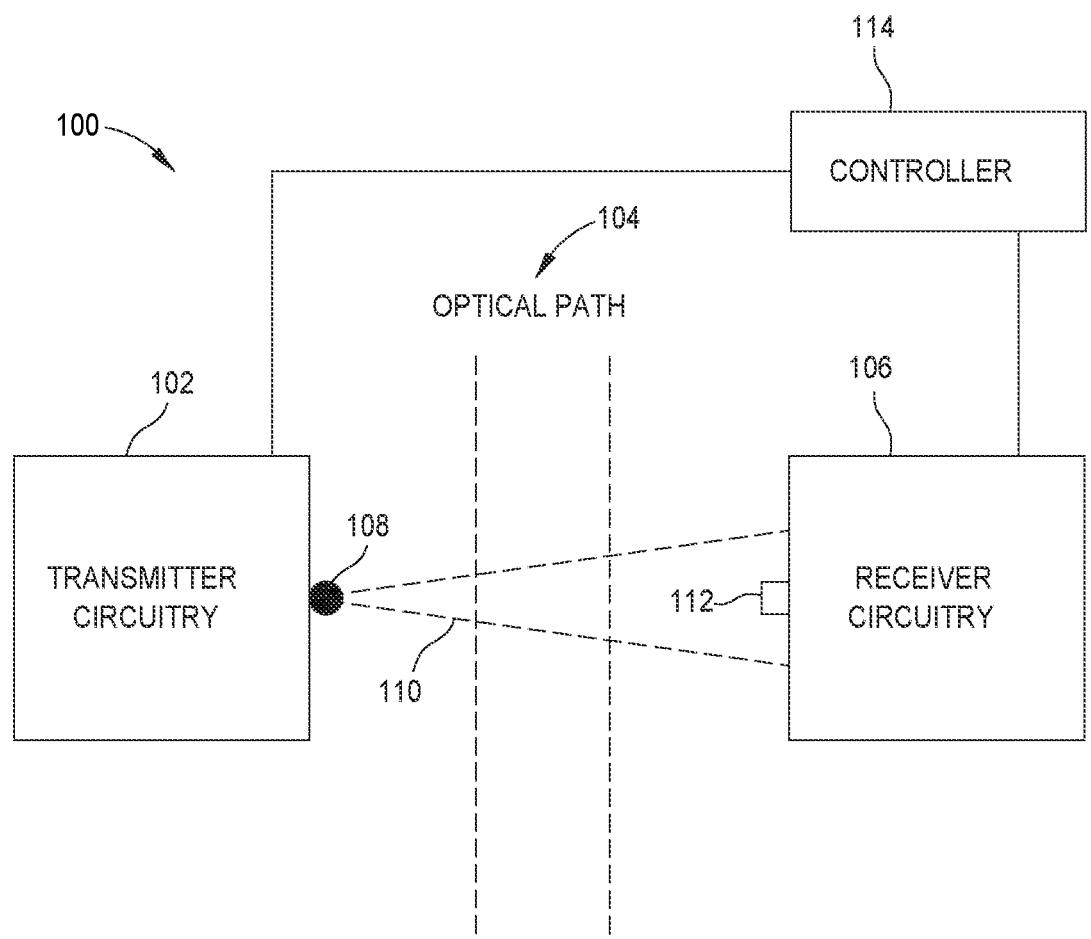
FIG. 1 illustrates a block diagram of an example system configured to determine a characteristic of an optical pathway, in accordance with certain embodiments.

Certain aspects provide mechanisms and techniques for determining one or more characteristics of an optical pathway. For example, such techniques may be used to determine if there is blockage in an optical pathway and/or indicate overall wellness of an optical pathway (e.g., an amount of decay due to ageing, effects of ambient temperature, etc.). In some cases, an optical pathway may correspond to a fluid pathway of a port within a pneumatically powered ophthalmic surgical machine (e.g., during a vitreoretinal procedure). Although certain aspects are described within the scope of a pneumatically powered ophthalmic surgical machine, it should be appreciated that techniques described herein can be used for determining one or more characteristics of any suitable optical pathway.

In certain aspects, transmitter and receiver circuitry of a photoelectric sensor system may be configured to perform photoelectric detection (such as detection at a port of a console, which may be referred to as port detection) of blockage within an optical pathway to provide readings of the optical pathway wellness. That is, the transmitter circuitry may be configured to generate a light output to be emitted through the optical pathway, the receiver circuitry may be configured to receive the emitted light to generate a voltage output corresponding to the received light. In this case, the intensity of the received light is based on the amount of blockage within the optical pathway, where more blockage would induce a less intense beam of light being received. Therefore, it follows that more blockage would induce a decreased voltage output generated by the receiver circuitry. Certain aspects are described herein with an LED as generating a light output, and a photodiode as receiving the light output, however, it should be noted that other suitable components may similarly be used.

In some photoelectric sensor implementations (whether interruptive or reflective in nature), there is a relatively high ratio of analog signal (or voltage) output level at the receiver circuitry between when the sensed object (e.g., blockage) is present in the optical pathway between the transmitter and the receiver and when the sensed object is absent in the optical pathway. For example, at a fixed LED current level, for example, a high ratio (e.g., 200:1 based on voltages 20V (Volts) and 0.1V) between the absence and presence of blockage can help ensure accurate differentiation of whether a pathway is in fact blocked or clear. In other words, the voltage output level at the receiver when the path is clear may be, for example, 200 times greater than the voltage output level at the receiver when the path is blocked. This high ratio is desirable since physical aspects of a photoelectric sensor (e.g., LED degradation, misaligned optics, and/or cloudy optics) may cause variation in the LED output regardless of blockage in the optical pathway between the transmitter and the receiver. However, even though a high signal ratio is helpful, the voltage output level can still vary considerably over a relatively wide voltage range, which may extend above the saturation voltage (e.g., 12V) of an amplifier at the receiver. Thus, some voltage outputs at the receiver indicating a clear path may become clipped at that saturation voltage. In this situation, fully accurate determinations of the overall optical pathway wellness may not be possible. This is because even if the optical pathway appears clear based on the output voltage at the receiver for a particular current level input to the LED at the transmitter, there may still exist some blockage that is not otherwise indicated by the output voltage level of the photoelectric sensor.

Accordingly, in certain aspects, transmitter and receiver circuitry described herein may be configured to perform photoelectric detection to determine a characteristic of an optical pathway using voltage output levels at the receiver circuitry while adjusting one or more of a gain at the receiver circuitry or a current input to an LED at the transmitter circuitry. For example, certain aspects may advantageously provide techniques for more accurate readings of optical pathway wellness.

In certain aspects, light may be emitted in an increasing fashion from an LED through an optical pathway, based on an increasing current input to the LED, during a time period that starts at a first time. The light output may be received and converted to a voltage output to determine a second time during the time period when the voltage output crosses a threshold. Then, a characteristic of the optical pathway (e.g., an amount of blockage and/or a wellness of the LED and a photodiode that receives the LED light output) may be determined based on a difference between the first time and the second time.

In certain aspects, light may be emitted from an LED (e.g., based on a constant current input to the LED) through an optical pathway during a time period that starts at a first time. The light may be received and converted to a voltage output varied by a changing gain of an amplifier to determine a second time during the time period when the voltage output crosses a threshold. Then, a characteristic of the optical pathway (e.g., an amount of blockage and/or a wellness of the LED and a photodiode that receives the LED light output) may be determined based on a difference between the first time and the second time.

In certain aspects, a current input may be applied to an LED and the output of the LED may be received and converted to a voltage output. It may be determined whether the voltage output is greater than a first threshold, and, when the voltage output is greater than the first threshold, a different current input (e.g., less than the first current input) may be applied to the LED for emission and reception/conversion. Then, it may be determined whether the voltage output is greater than a different threshold (e.g., less than the first threshold), and a characteristic of the optical pathway can be determined based on whether the voltage output is greater than the second threshold.

In certain aspects, a current input may be applied to an LED and the output of the LED may be received and converted to a voltage output while an amplifier of the receiver is configured with a first gain. It may be determined whether the voltage output is greater than a first threshold. When the voltage output is greater than the first threshold, the current input may be applied to the LED, and the output of the LED may be received and converted to a voltage output while the amplifier is configured with a different gain (e.g., less than the first gain). Then, it may be determined whether the voltage output is greater than a different threshold (e.g., less than the first threshold), and a characteristic of the optical pathway can be determined based on whether the voltage output is greater than the second threshold.

In some embodiments, the method(s) described herein may be implemented in a pneumatically powered ophthalmic surgical machine to perform port detection. More generally, aspects described herein may be used in any photoelectric sensor application, where it is desirable to monitor not only the actual detection of an item (e.g., blockage) but also the quality of the total sensor path and any potential degradation of the sensor path (e.g., having electronic circuitry, optical elements, etc.).

While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with various other embodiments discussed herein. In similar fashion, while exemplary embodiments may be discussed below as device, instrument, or method embodiments it should be understood that such exemplary embodiments can be implemented in various devices, instruments, and methods.

Example LED Detection Circuit and Methods of Operation

Certain aspects of the present disclosure provide techniques for determining whether optical pathways are blocked. In certain aspects, the circuit(s) described herein may be implemented in a pneumatically powered ophthalmic surgical machine to perform port detection. More generally, aspects, methods, and techniques described herein may be used in any photoelectric sensor application where it is desirable to monitor not only the actual detection of an item (e.g., blockage) but also the quality of the total sensor path (e.g., having electronic circuitry, optical elements, etc.).

As described above, a high signal ratio between a voltage output at a receiver indicating no blockage and a voltage output indicating blockage of an optical pathway can be helpful, but the relatively wide range of possible voltage outputs may cause the saturation voltage (e.g., 12V) of an amplifier to be reached and even exceeded. Thus, some voltage outputs at a receiver indicating a clear path of an optical pathway may become clipped at that saturation voltage. In other words, a received LED signal that generates a first voltage output (e.g., 16V) may be regarded the same as another received LED signal that generates a second lesser (or greater) voltage output (e.g., 12V) despite the LED signals being indicative of different pathway wellness. In this situation, fully accurate determinations of the overall optical pathway wellness may not be possible, because even if the optical pathway appears clear for a particular current level applied to the LED, there may still exist some blockage that is not otherwise indicated by the output voltage level of the photoelectric sensor.

Accordingly, certain aspects provide techniques for improved detection in a photoelectric sensor application to determine one or more characteristics of an optical pathway. For example, certain aspects provide for one or more techniques implemented in transmitter circuitry and/or receiver circuitry described to leverage a varied current and/or gain, as described in more detail herein.

FIG. 1 illustrates a block diagram of an example system 100 configured to determine a characteristic of an optical pathway, in accordance with certain embodiments. In some cases, the system 100 may be implemented in one of the ports RF1, RF2, RF3, RF4, and/or RF5 in the schematic 200 of a pneumatic module of FIG. 2. Referring back to FIG. 1, the system 100 includes transmitter circuitry 102, an optical pathway 104, receiver circuitry 106, an LED 108 configured to propagate light 110, a light detection element 112 (e.g., a photodiode, a phototransistor, a photoresistor, etc.), and a controller 114. The transmitter circuitry 102 may be configured to provide current to the LED 108 to propagate the beam of light 110, as shown, through the optical pathway 104 for the receiver circuitry 106 to receive and convert that received light 110 to a voltage output. The controller 114 may be configured to control voltage and/or current inputs/outputs for each of the transmitter circuitry 102 and/or the receiver circuitry 106. Furthermore, the controller 114 may be configured to sample the voltage output generated by the receiver circuitry 106. In certain aspects, the optical pathway 104 corresponds to a path across one of the ports RF1, RF2, RF3, RF4, and/or RF5 in the schematic 200 of a pneumatic module of FIG. 2. In particular, the ports RF1, RF2, RF3, RF4, and/or RF5 may correspond to a cross-section of a fluid pathway in a surgical console.

As described above, various configurations and/or techniques may be implemented in the transmitter circuitry 102 and/or the receiver circuitry 106 for improved port detection. For example, the transmitter circuitry 102 may be configured to generate an increasing current input to the LED 108 (e.g., via circuitry described herein or any suitable current increasing circuit) such that the light 110 output from the LED 108 increases in a similar fashion. As the light 110 output from the LED 108 changes (e.g., increases), the voltage output in the receiver circuitry 106 may change (e.g., increase) in a fashion coordinate with the light 110 intensity through the optical pathway 104.

In certain aspects, the increase in current input to the LED 108 may be during a time period starting at a first time, where the receiver circuitry 106 may receive the light 110 via the light detection element 112 and convert the received light 110 to a voltage output. Additionally, the controller 114 may be configured to determine a time during the time period when the voltage output crosses a threshold. For example, the threshold voltage may be the saturation voltage of an amplifier included in the receiver circuitry 106, or a voltage level just below the saturation voltage of the amplifier. Based on a time difference between the time the voltage output of the light detection element 112 crosses the threshold and the start time of the current increase, a characteristic of the optical pathway 104 (e.g., an amount of blockage or overall wellness/decay) can be determined. For example, a gain (or slope) may be associated with the current increase, and similarly a gain (or slope) may correspondingly be associated with the voltage output. The greater the gain or slope, the shorter the time difference between the time the voltage output of the light detection element 112 crosses the threshold and the start time of the current increase. Further, as discussed further herein, the greater the gain or slope, the greater the estimated unclipped voltage output level (above the saturation voltage of the amplifier) at the receiver circuitry 106. Accordingly, a shorter time difference may be indicative of a greater estimated unclipped voltage output level, and accordingly, less blockage and/or obstruction of the optical pathway 104. Accordingly, controller 114 may be configured to compare the time difference to one or more thresholds, and if the time difference is greater than a particular threshold, it may indicate a particular level of blockage and/or obstruction of the optical pathway 104 associated with the particular threshold. Thus, by using a varied current input to the LED and measuring a voltage output based on the light output of the LED, the wellness of the optical pathway can be ascertained without incurring ambiguity from exceeding the saturation voltage of an amplifier included in the receiver circuitry 106.

Figure 3A:
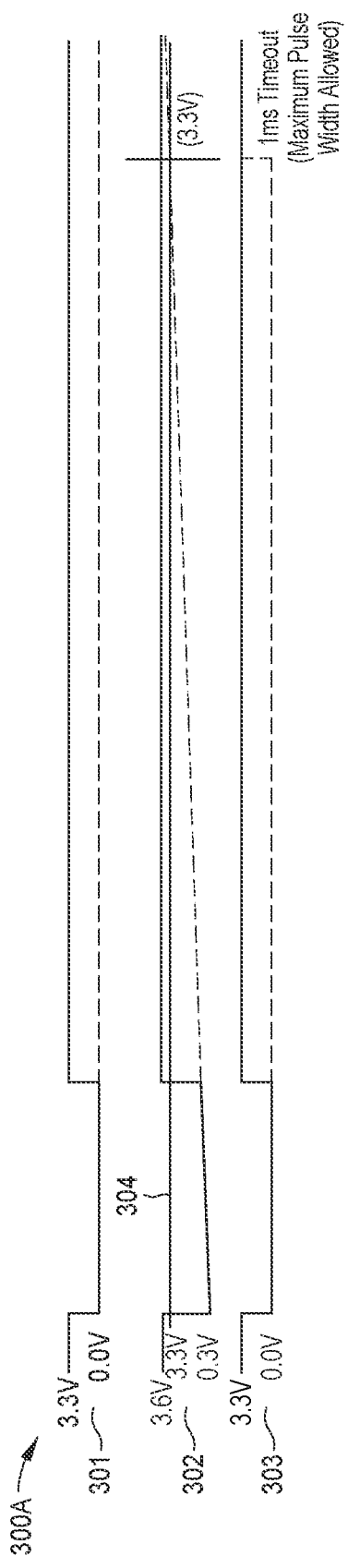
FIGS. 3A-3C illustrate various timing diagrams associated with voltage levels and/or various gains of circuit input or light emitting diode (LED) output, in accordance with certain embodiments.
Figure 3B:
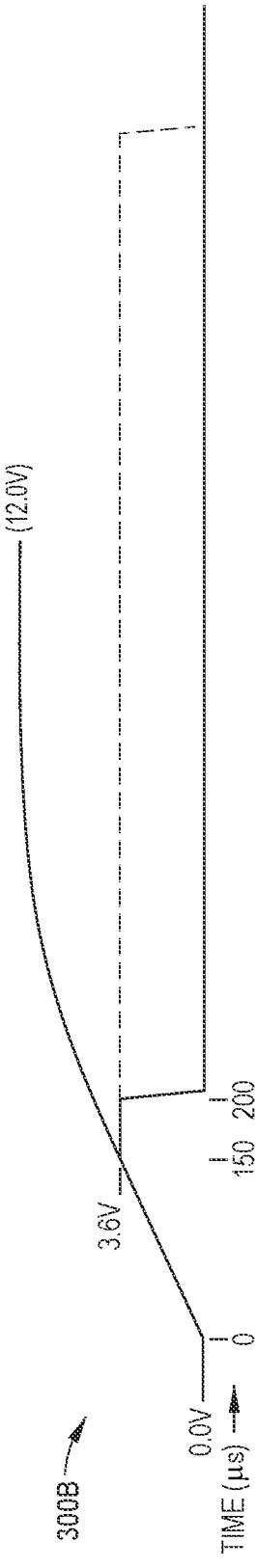
Figure 3C:
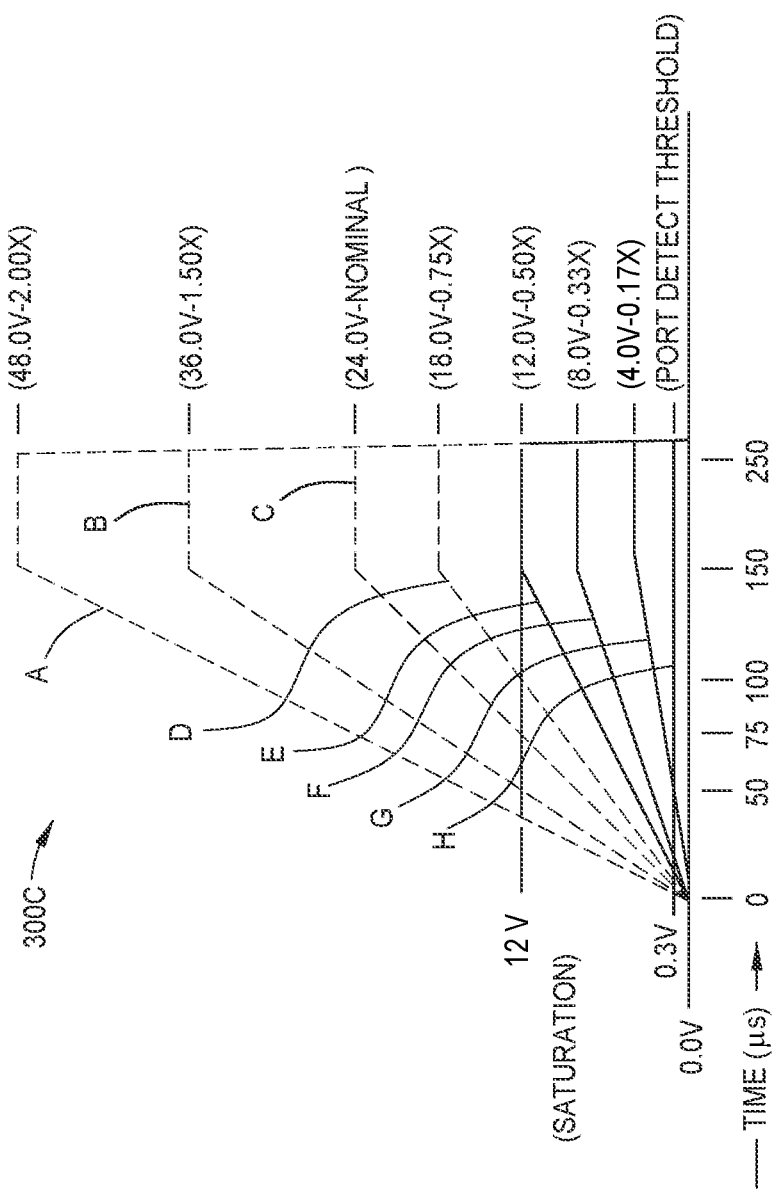
Figure 8A:
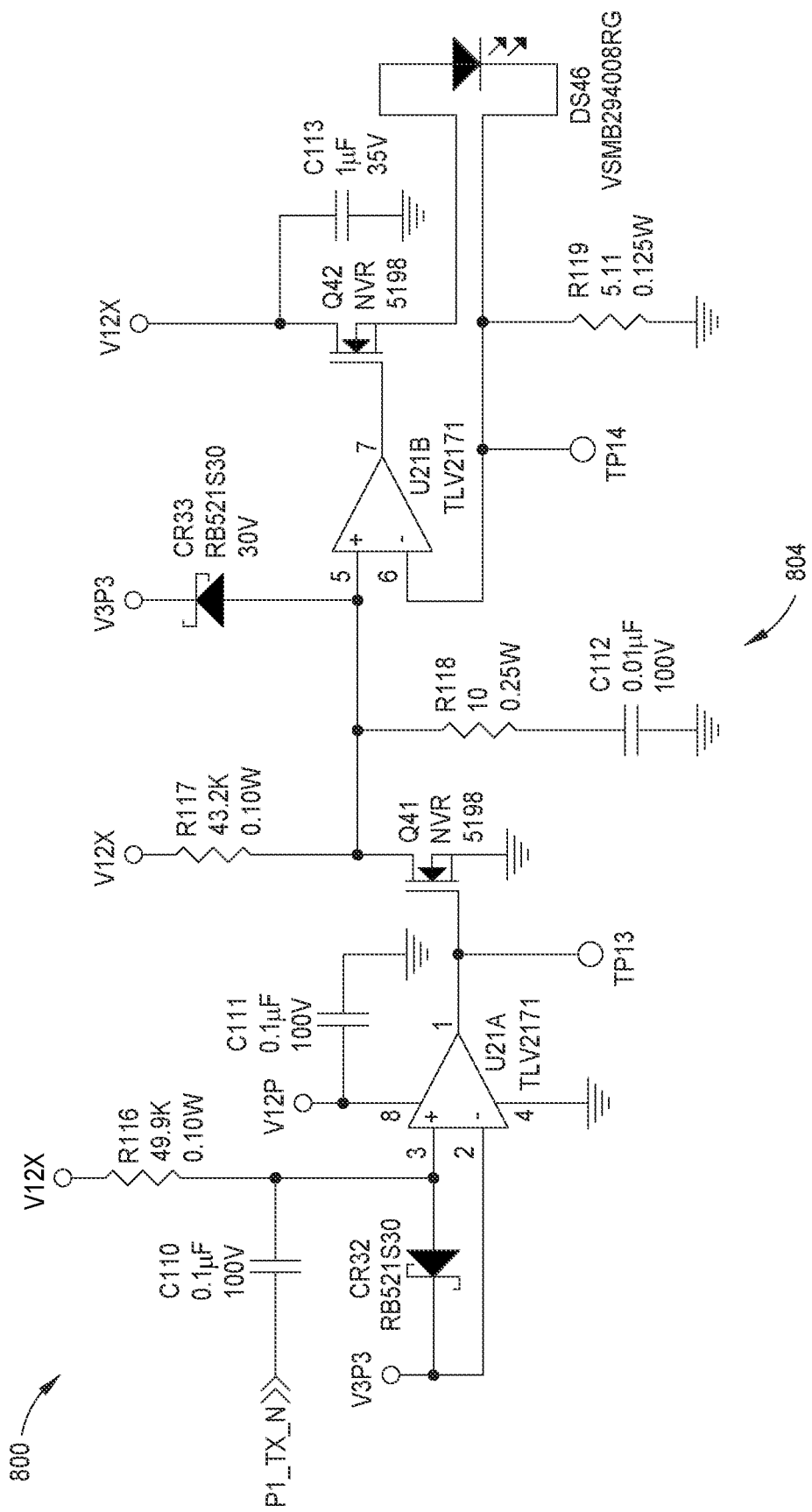
FIGS. 8A-8B illustrate an example circuit diagram, in accordance with certain embodiments.

As an illustrative example, FIGS. 3A-3C illustrate various timing diagrams associated with voltage levels and/or various gains of circuit input or LED output, in accordance with certain embodiments. In particular, FIG. 3A is a set of graphs 300A of example timing diagrams 301, 302, 303 associated with various components of transmitter circuitry (e.g., the transmitter circuitry 102 of FIG. 1). For example, an ON pulse (e.g., the timing diagram 301 pulse width from a falling edge to a rising edge) may be applied to an LED (e.g., the LED 108 of FIG. 1) for a period of time on a periodic basis (e.g., for 200 μs (microseconds) every 200 ms (milliseconds)). This ON pulse may be generated by the falling edge of the timing diagram 301 (e.g., from 3V to 0V), triggering falling edges for the timing diagrams 302 and 303, as shown. For example, the timing diagram 301 may correspond to an input of the transmitter circuitry, and each of the timing diagrams 302 and 303 illustrates a limit on the duration that current is applied to the LED by providing a timeout (such as at 1 ms). As shown, when the voltage level of the timing diagram 301 drops from 3.3V to 0V, the voltage level of the timing diagram 302 similarly drops from 3.6V to 0.3V. In this case, the output state of the amplifier acting as a comparator represented by the timing diagram 303 may be based on a comparison of the voltage level depicted in the timing diagram 302 and a threshold voltage 304 (e.g., 3.3V). As shown, when the voltage level of the timing diagram 302 is below the threshold voltage 304, the output state of the amplifier is logical low (e.g., 0.0V meaning that Q41 as shown in FIG. 8A is OFF).

As shown in FIG. 3B, which is a graph 300B of an example increasing current input (e.g., the increasing current input described with respect to the transmitter circuitry 102 of FIG. 1), the falling edge of the timing diagram 303 indicating the ON pulse triggers a ramp-up interval (e.g., 150 μs in duration) to a current (or voltage) level that provides the desired maximum or plateau current (e.g., for 50 μs) to an LED (e.g., the LED 108 of FIG. 1). In certain aspects, a controller (e.g., the controller 114 of FIG. 1) may include an analog-to-digital converter (ADC) synchronized with the LED ON pulse such that as soon as the current begins to ramp up, the ADC of the controller may sample a voltage output of receiver circuitry (e.g., the receiver circuitry 106) periodically within the ON pulse duration (e.g., every 5 μs such that 40 samples are taken over the 200 μs total duration).

FIG. 3C is a set of graphs 300C illustrating example light detection element received voltage output sampled over an ON pulse duration. As shown, the graphs 300C includes lines A, B, C, D, E, F, G, and H (A-H), where each of the lines A-H correspond to various increases in voltage output based on the current input of the graph 300B of FIG. 3B. Although eight lines are shown in FIG. 3C, it should be appreciated that many more lines may exist and correspond to various current inputs. As illustrated, each of the lines A-E cross a saturation voltage line (e.g., 12V) at various points, while the lines F-H do not reach the saturation voltage line. Thus, the crossing points for each of the lines A-H may indicate a characteristic of an optical pathway (e.g., the optical pathway 104 of FIG. 1). For example, lines A-H may indicate a degree of blockage, where A is the least blocked, and H is the most blocked. For example, the crossing point of the lines A-E may generally indicate the optical pathway is clear according to a threshold (wherein the threshold may be different for different embodiments), where the line A indicates the least amount of blockage, while the crossing point of the lines F-H may generally indicate the optical pathway is blocked according to the threshold, where the line H indicates the most amount of blockage.

As can be seen in FIG. 3C, the point of intersection or "knee" shifts (e.g., left or right relative to the line C) due to gain variations (e.g., based on levels of blockage) in the sensing path. For example, at nominal gain (e.g., unity gain) represented by line C (e.g., with an expected plateau level of what would be 24.0V), the ramp up reaches the 12.0V saturation level at 75 μs, which may be considered the nominal location for the ramp-to-plateau knee. Relative to the nominal plateau line C, with an increase in overall sensing path gain (e.g., less blockage in the pathway), the projected voltage output would increase in amplitude (e.g., the slope/gain is increased) and the ramp-to-plateau knee may move to the left, as represented by, for example, line B (e.g., 1.50 gain and/or 36.0V as the expected plateau) and/or line A (e.g., 2.00 gain and/or 48.0V expected plateau). Conversely, if overall sensing path gain should decrease (e.g., more blockage in the pathway), the projected and the actual voltage output will follow lines D-H as gain decreases further due to increasing blockage in the optical pathway.

However, as explained above, a voltage output being at or above the saturation voltage may not be sufficient to determine overall optical path wellness since some of the voltage outputs may become clipped (e.g., shown by lines A-D). Thus, the techniques performed by the controller 114 described above may help determine a time difference between when the increasing current input starts and when the voltage output crosses the threshold (e.g., saturation) voltage level. Such time difference may be indicative of a slope, such as corresponding to one of the lines A-H. Furthermore, the optical pathway wellness could be determined based on whether the voltage output reaches the saturation voltage level too late (e.g., after 75 μs). In particular, if the time difference corresponds to any of the lines D-H, the overall wellness of the optical pathway can be considered worsening and/or blocked. Conversely, a time difference corresponding to the lines A-C may indicate that the optical pathway is clear and/or the wellness could be improved. Further, if the time difference begins to increase, it can be determined the optical pathway, though currently clear, is degrading. Accordingly, remedial action can be taken before the optical pathway is blocked to a level that is more severe.

Referring back to FIG. 1, in certain aspects, a gain of an amplifier included in the receiver circuitry 106 may be varied during a time period that starts at a first time to vary the voltage output of the light detection element 112. That is, for a current input, the gain of the amplifier may be varied to two or more different values, and the voltage output may be used to determine a second time when the voltage output of the light detection element 112 crosses a threshold. Therefore, instead of (or in addition to) changing the current input to the LED 108 to change the voltage output, the gain of an amplifier can be varied (e.g., by varying a resistance coupled to the amplifier, such as using a varistor, switches to selectively couple one or more resistors, etc.) to determine when then voltage output crosses a threshold (e.g., the saturation voltage described in FIG. 3C).

Referring again to FIG. 3C, each of lines A-H may be defined by two points. In terms of FIG. 3C, the two points are a time value on the x-axis and a voltage output on the y-axis. The time value, as discussed, may be indicative of a particular current input level to the LED 108 and/or a particular gain applied to an amplifier coupled to light detection element 112. Accordingly, each of lines A-H may be defined by two points, 1) (a first current input and/or amplifier gain, a first voltage output); and 2) (a second current input and/or amplifier gain, a second voltage output). Further, at any given time value, and accordingly current input and/or amplifier gain, the voltage output will correspond to a particular one of lines A-H, so long as the voltage output is below the measurable saturation voltage.

Therefore, in certain aspects, multiple thresholds (e.g., voltage thresholds) may be implemented to determine the characteristic of the optical pathway 104. For example, one voltage threshold may correspond to the saturation voltage and a sufficiently high current input and/or amplifier gain may be applied. If the output voltage exceeds the threshold while the sufficiently high current input and/or amplifier gain is applied, that may be indicative of clipping (e.g., corresponding to any of lines A-E), meaning another current input and/or amplifier gain should be used and the voltage output compared to another threshold to determine the characteristic of the optical pathway 104 (e.g., which of lines A-E the output is correlated to). For example, the current input and/or amplifier gain may be set to a value correlated with 50 μs as shown in FIG. 3C, and the threshold may be set to the output voltage of line C at 50 μs as shown in FIG. 3C. Accordingly, should the new output voltage exceed the new threshold under such circumstances, the optical pathway 104 may be determined to be sufficiently well, as the output voltage corresponds to one of lines A-C, and not to one of lines D-E (which would correspond to an output voltage below the new threshold).

Accordingly, in certain cases, for a first current input applied to the LED 108, the output of the LED may be received and converted to a voltage output. It may be determined whether the voltage output is greater than (or equal to) a first threshold (e.g., a saturation threshold of 12V as shown in FIG. 3C), and, when the voltage output is greater than the first threshold, a different current input (e.g., less than the first current input) may be applied to the LED 108 and converted to a voltage output. Then, it may be determined whether the voltage output is greater than a second threshold (e.g., a less than the first threshold). A characteristic of the optical pathway 104 may be determined based on whether the voltage output is greater than the second threshold for the second current input, as discussed.

In certain aspects, a current input is applied to the LED 108, and the output of the LED may be received and converted based on an amplifier having a first gain. It may be determined whether the voltage output is greater than (or equal to) a first threshold (e.g., saturation threshold of 12V as shown in FIG. 3C), and, when the voltage output is greater than the first threshold, a different gain greater than the first gain may be applied to the amplifier for determining a second voltage output. Then, it may be determined whether the second voltage output is greater than a second threshold (e.g., less than the first threshold). A characteristic of the optical pathway 104 may be determined based on whether the voltage output is greater than the second threshold for the second gain, as discussed.

Figure 4:
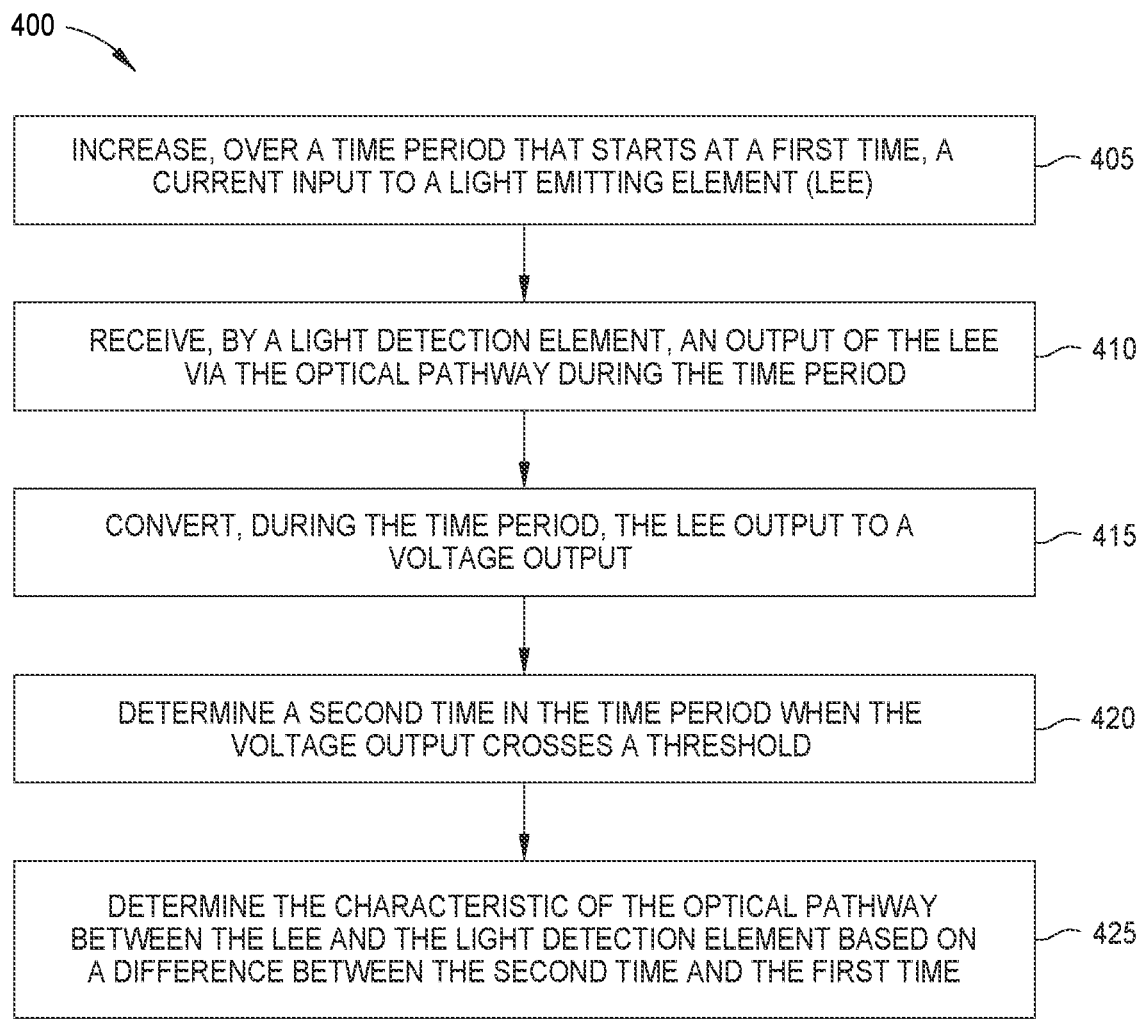
FIG. 4 illustrates a flow diagram of example operations for determining a characteristic of an optical pathway, in accordance with certain embodiments.

FIG. 4 is a flow diagram illustrating example operations 400 for determining a characteristic of an optical pathway (e.g., the optical pathway 104 of FIG. 1) corresponding to a fluid pathway of a device, in accordance with certain aspects of the present disclosure. The operations 400 may be performed, for example, by a system (e.g., such as the system 100, shown in FIG. 1).

The operations begin, at 405, by increasing, over a time period that starts at a first time, a current input to a light emitting element (LEE) (e.g., the LED 108 of FIG. 1).

At 410, the system receives, by a photodiode (or other light detection element such as light detection element 112 of FIG. 1), an output of the LEE via the optical pathway during the time period.

At 415, the system converts, during the time period, the LEE output to a voltage output.

At 420, the system determines a second time in the time period when the voltage output crosses a threshold.

At 425, the system determines the characteristic of the optical pathway between the LED and the photodiode based on a difference between the second time and the first time.

In certain aspects of the operations 400, the characteristic of the optical pathway includes an amount of blockage within the optical pathway.

In certain aspects of the operations 400, the threshold is a saturation voltage of an amplifier coupled to the light detection element.

In certain aspects of the operations 400, determining the characteristic of the optical pathway between the LEE and the light detection element based on the difference between the second time and the first time includes determining whether the difference is greater than a time value. In this case, the operations 400 may further include, when the difference is greater than the time value, providing an indication of blockage of the optical pathway.

Figure 2:
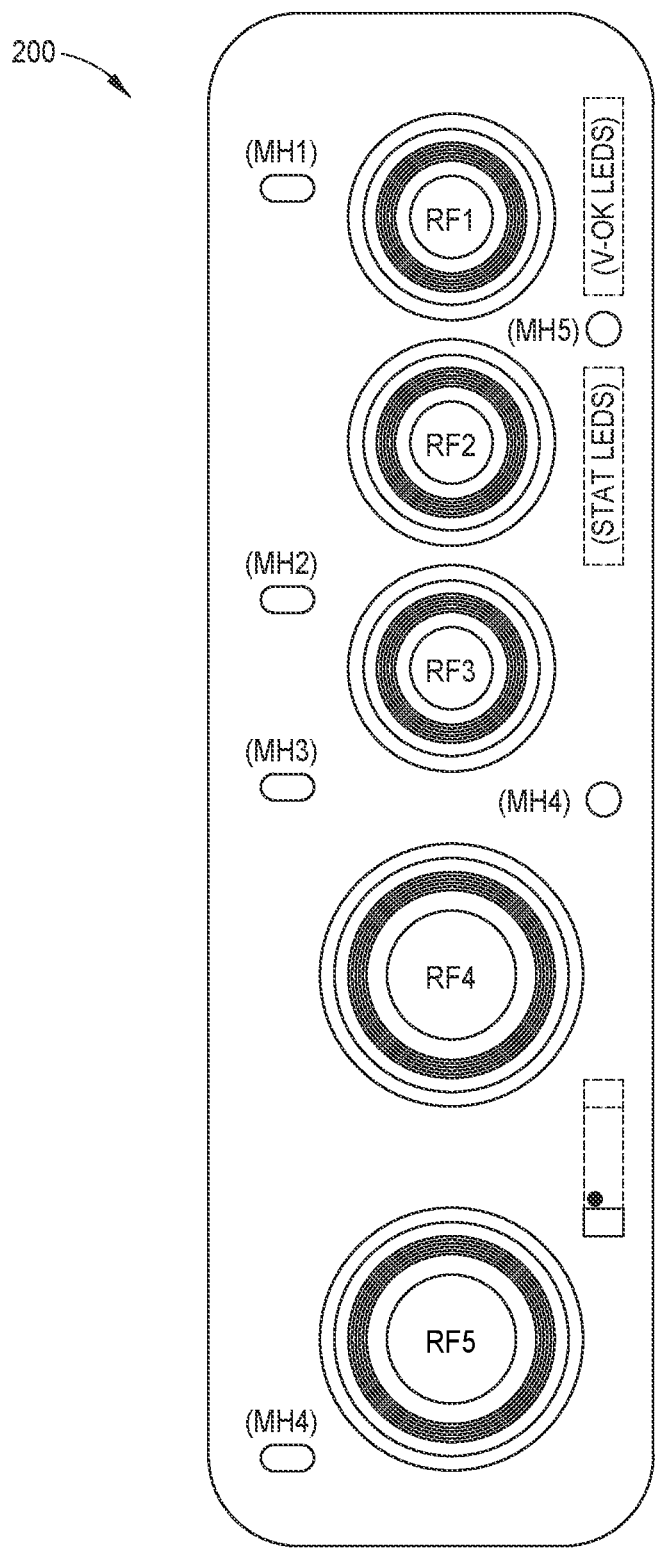
FIG. 2 illustrates a schematic of five pneumatic connectors or "ports" of a pneumatic module, in accordance with certain embodiments.

In certain aspects of the operations 400, the optical pathway is disposed within a pneumatic port (e.g., one of the ports RF1, RF2, RF3, RF4, or RF5 of FIG. 2).

In certain aspects of the operations 400, the voltage input to the LEE is increased by using a resistor capacitor (RC) circuit having a time constant associated with the time period.

Figure 5:
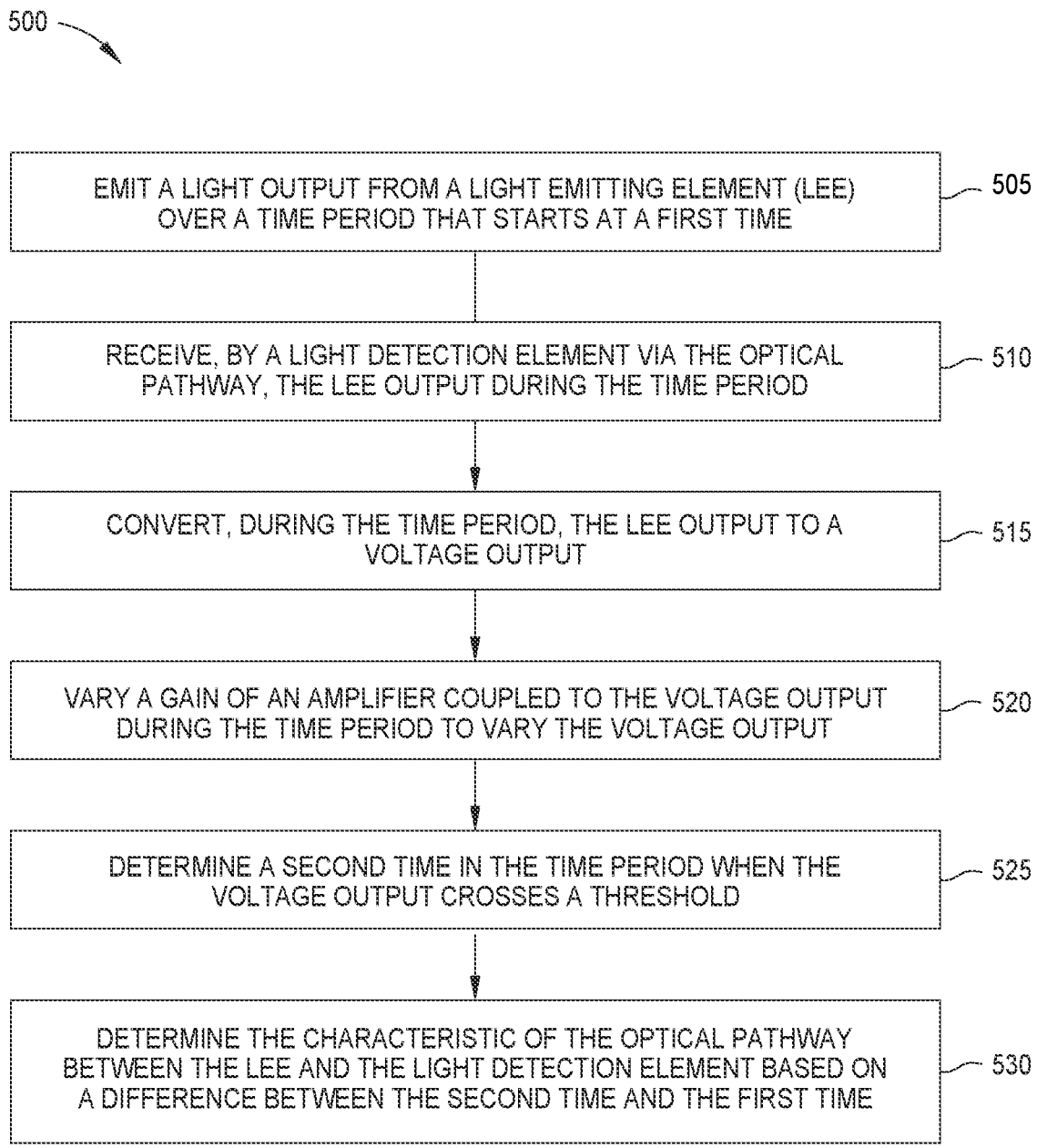
FIG. 5 illustrates another flow diagram of example operations for determining a characteristic of an optical pathway, in accordance with certain embodiments.

FIG. 5 is a flow diagram illustrating example operations 500 for determining a characteristic of an optical pathway (e.g., the optical pathway 104 of FIG. 1) corresponding to a fluid pathway of a medical device, in accordance with certain aspects of the present disclosure. The operations 500 may be performed, for example, by a system (e.g., such as the system 100, shown in FIG. 1).

The operations begin, at 505, by emitting a light output from an LEE (e.g., the LED 108 of FIG. 1) over a time period that starts at a first time.

At 510, the system receives, by a photodiode (or other light detection element such as the light detection element 112 of FIG. 1) via the optical pathway, the LEE output during the time period.

At 515, the system converts, during the time period, the LEE output to a voltage output.

At 520, the system varies a gain of an amplifier coupled to the voltage output during the time period to vary the voltage output.

At 525, the system determines a second time in the time period when the voltage output crosses a threshold.

At 530, the system determines the characteristic of the optical pathway between the LEE and the light detection element based on a difference between the second time and the first time.

In certain aspects of the operations 500, the characteristic of the optical pathway includes an amount of blockage within the optical pathway.

In certain aspects of the operations 500, varying the gain of the amplifier includes varying a resistance coupled to the amplifier.

In certain aspects of the operations 500, the threshold is a saturation voltage of the amplifier.

Figure 6:
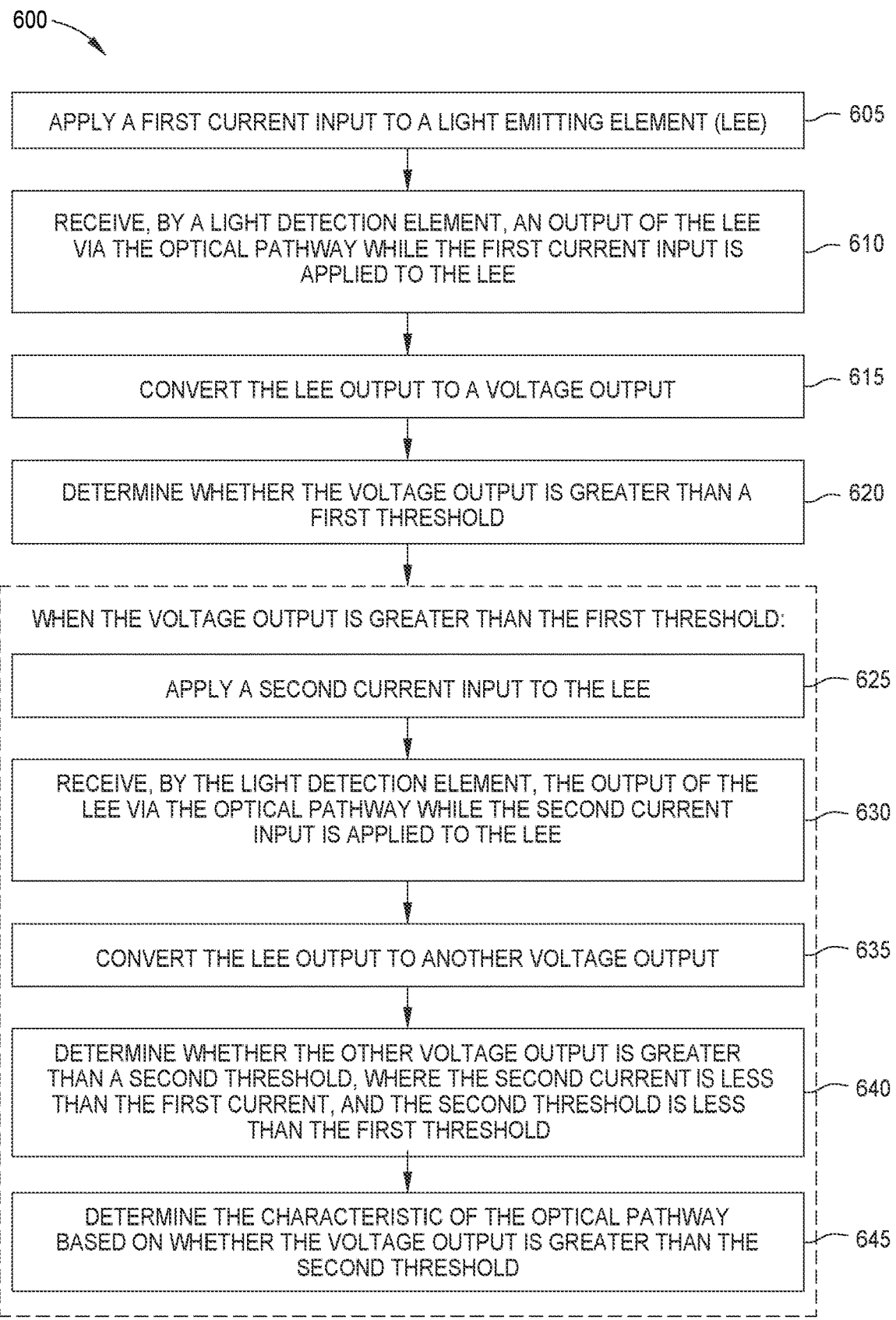
FIG. 6 illustrates another flow diagram of example operations for determining a characteristic of an optical pathway, in accordance with certain embodiments.

FIG. 6 is a flow diagram illustrating example operations 600 for determining a characteristic of an optical pathway (e.g., the optical pathway 104 of FIG. 1) corresponding to a fluid pathway of a medical device, in accordance with certain aspects of the present disclosure. The operations 600 may be performed, for example, by a system (e.g., such as the system 100, shown in FIG. 1).

The operations begin, at 605, by applying a first current input to an LEE (e.g., the LED 108 of FIG. 1).

At 610, the system receives, by a photodiode (or other light detection element such as the light detection element 112 of FIG. 1), an output of the LEE via the optical pathway while the first current input is applied to the LEE.

At 615, the system converts the LEE output to a voltage output.

At 620, the system determines whether the voltage output is greater than a first threshold.

As shown, the operations 625-645 occur when the voltage output is greater than the first threshold.

At 625, the system applies a second current input to the LEE.

At 630, the system receives, by the light detection element, the output of the LEE via the optical pathway while the second current input is applied to the LEE.

At 635, the system converts the LEE output to another voltage output.

At 640, the system determines whether the other voltage output is greater than a second threshold, where the second current is less than first current, and the second threshold is less than the first threshold.

At 645, the system determines the characteristic of the optical pathway based on whether the other voltage output is greater than the second threshold.

In certain aspects of the operations 600, the characteristic of the optical pathway is an amount of blockage within the optical pathway.

In certain aspects of the operations 600, the first voltage output is a saturation voltage of an amplifier coupled to the light detection element.

In certain aspects, the operations 600 further include, when the other output voltage is less than the second threshold, providing an indication of blockage of the optical pathway.

In certain aspects of the operations 600, the optical pathway is disposed within a pneumatic port.

Figure 7:
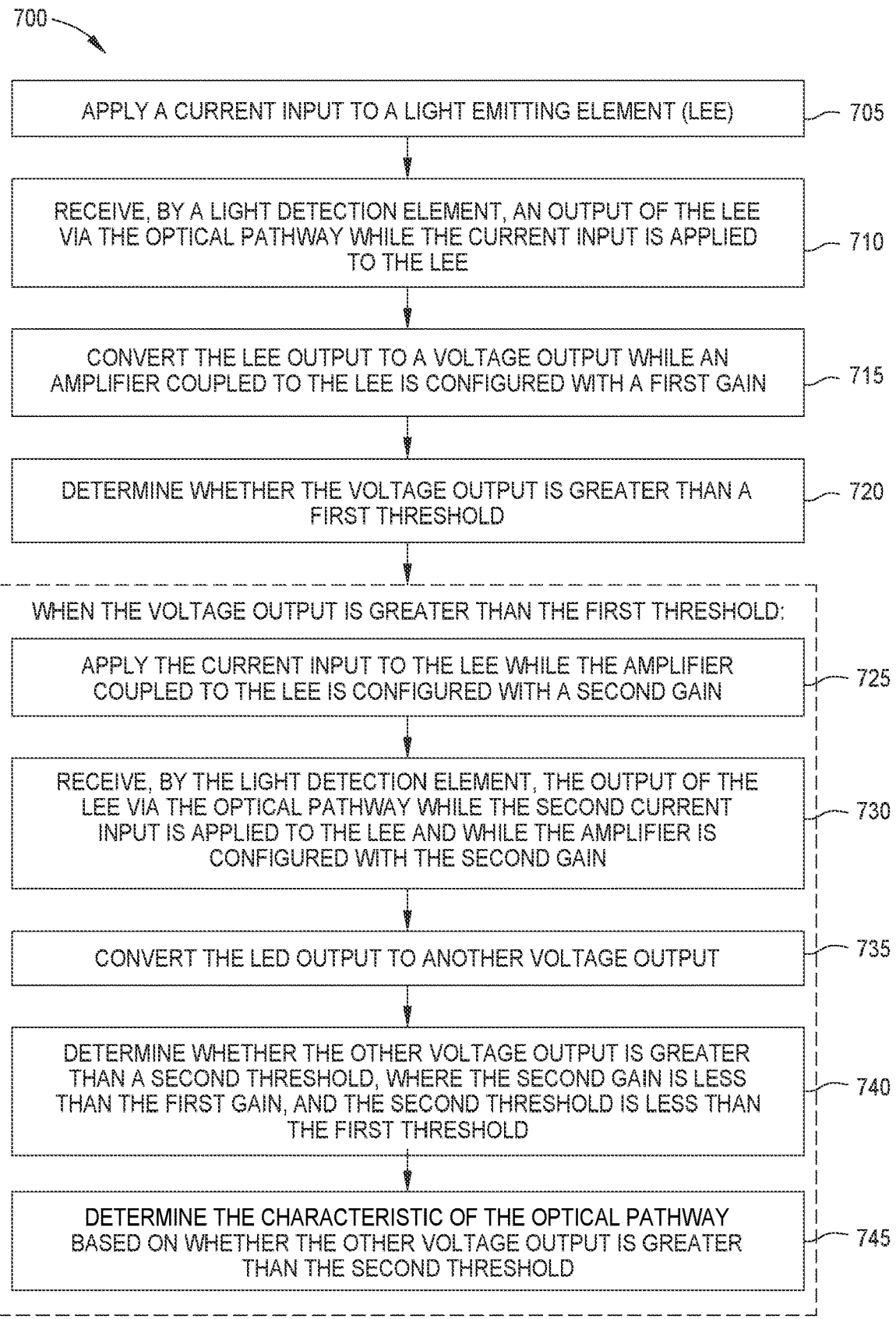
FIG. 7 illustrates yet another flow diagram of example operations for determining a characteristic of an optical pathway, in accordance with certain embodiments.

FIG. 7 is a flow diagram illustrating example operations 700 for determining a characteristic of an optical pathway (e.g., the optical pathway 104 of FIG. 1) corresponding to a fluid pathway of a medical device, in accordance with certain aspects of the present disclosure. The operations 700 may be performed, for example, by a system (e.g., such as the system 100, shown in FIG. 1).

The operations begin, at 705, by applying a current input to an LEE (e.g., the LED 108 of FIG. 1).

At 710, the system receives, by a photodiode (or other light detection element such as the light detection element 112 of FIG. 1), an output of the LEE via the optical pathway while the current input is applied to the LEE.

At 715, the system converts the LEE output to a voltage output while an amplifier coupled to the LEE is configured with a first gain.

At 720, the system determines whether the voltage output is greater than a first threshold.

As shown, the operations 725-745 occur when the voltage output is greater than the first threshold.

At 725, the system applies the current input to the LEE while the amplifier coupled to the LEE is configured with a second gain.

At 730, the system receives, by the light detection element, the output of the LEE via the optical pathway while the current input is applied to the LEE and while the amplifier is configured with the second gain.

At 735, the system converts the LEE output to another voltage output.

At 740, the system determines whether the other voltage output is greater than a second threshold, where the second gain is less than first gain, and the second threshold is less than the first threshold.

At 745, the system determines the characteristic of the optical pathway based on whether the other voltage output is greater than the second threshold.

In certain aspects of the operations 700, the characteristic of the optical pathway is an amount of blockage within the optical pathway.

In certain aspects of the operations 700, varying the gain of the amplifier includes varying a resistance coupled to the amplifier.

In certain aspects of the operations 700, the first threshold is a saturation voltage of the amplifier.

In certain aspects, the operations 700 further include, when the other output voltage is less than the second threshold, providing an indication of blockage of the optical pathway.

In certain aspects of the operations 700, the optical pathway is disposed within a pneumatic port.

Example Circuit System and Implementation

Figure 8B:
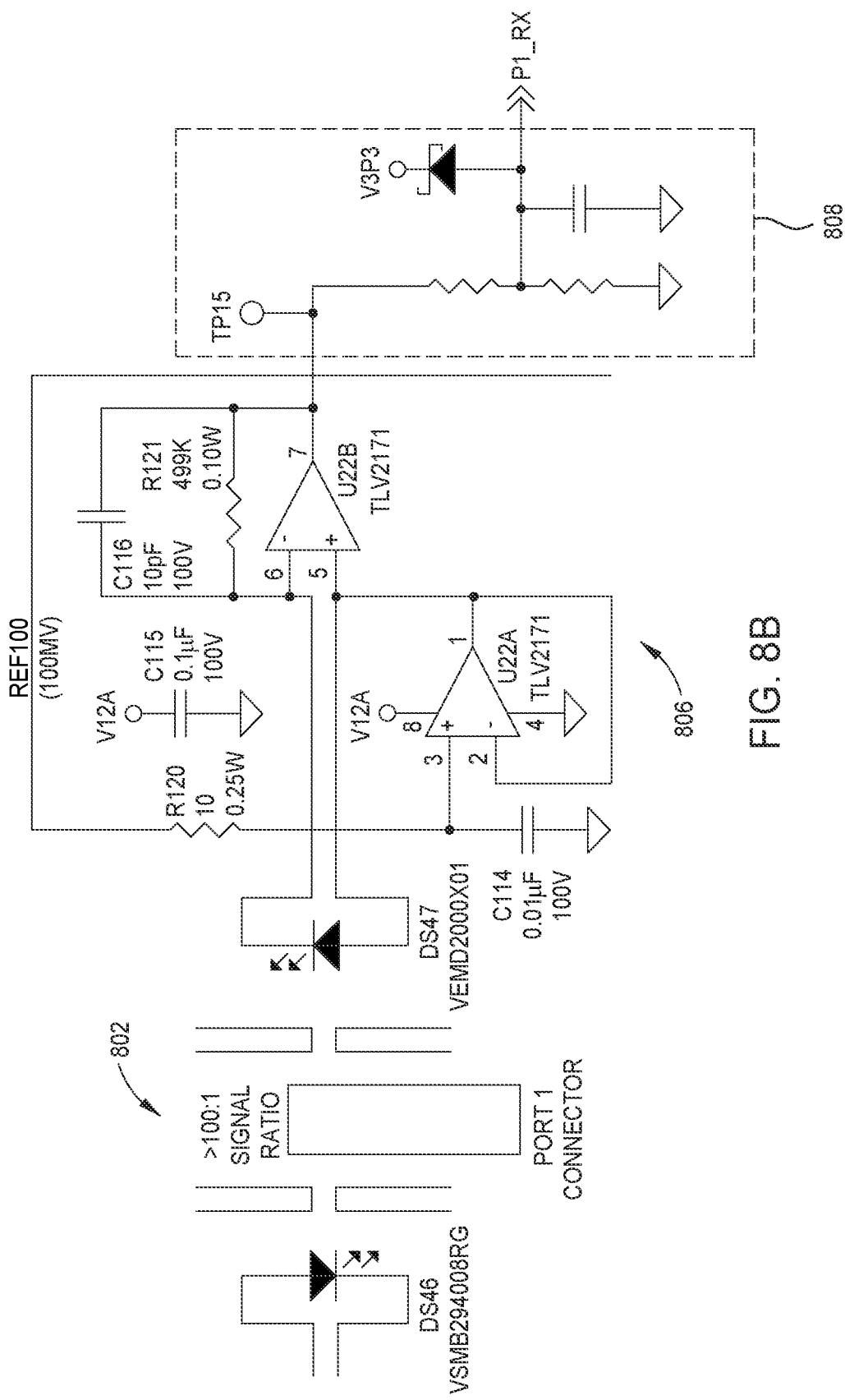

FIGS. 8A-8B collectively illustrate an example schematic for a circuit 800 for detecting any blockage in an optical pathway (e.g., the optical pathway 802 of FIG. 8B), in accordance with certain embodiments. Although only the circuit 800 is shown as an example circuit in which the methods and techniques described herein may be performed, it should be appreciated that the techniques described herein are not so limited to being accomplished by only the circuit 800. In other words, the circuit 800 may generally be configured to increase a current input to an LED, and other circuit configurations (e.g., a multiplexer configuration) that generate an increasing (ramped) voltage output may also be suitable.

The circuit 800 includes emitter (or transmitter) side circuitry 804 (e.g., corresponding to the transmitter circuitry 102 of FIG. 1) and detector (or receiver) side circuitry 806 (e.g., corresponding to the receiver circuitry 106 of FIG. 1), as shown in FIGS. 8A and 8B, respectively. The consumable is represented by the PORT 1 CONNECTOR between an LED emitter DS46 and detector DS47.

Referring to the circuit 800 in FIG. 8A, prior to the arrival of a falling edge for P1_TX_N (e.g., corresponding to the timing diagram 301 of FIG. 3A), current in resistor R116 is charging capacitor C110 up to the 12.0V supply voltage V12X. However, Schottky diode CR32 prevents such charge by steering the current from R116 into supply voltage V3P3 (e.g., of 3.3V). The supply voltage V3P3 is presumed capable of absorbing that current, and, if not, a dummy load can be added. Thus, the non-inverting input 3 of amplifier U21A (e.g., an operational amplifier) is at approximately 3.6V (e.g., 3.3V of supply plus the forward voltage (Vf) of the diode CR32=0.3V), and the output 1 of the amplifier U21A is HI at 12.0V. It should be noted that the amplifier U21A is being used as a comparator in this implementation.

With output 1 of the amplifier U21A being HI, the transistor Q41 is held in an ON state, and all current through the resistor R117 that would otherwise charge the capacitor C112 is shunted to GND. The relatively low on state resistance (e.g., $R_{DS,ON}$) of the transistor Q41 allows the non-inverting input 5 of the amplifier U22B to be practically zero, which keeps the emitter LED DS46 in an OFF state. Resistor R118 is not present for any waveform generation, but the resistor R118 does protect the transistor Q41 from overdrawing current when the time comes for the capacitor C112 to be discharged.

At the beginning of the P1_TX_N pulse (e.g., the falling edge of the graph 301 as shown in FIG. 3A), the 3.3V-to-0.0V transition of P1_TX_N causes a 3.6V-to-0.3V transition at the non-inverting input 3 of the amplifier U21A (e.g., due to the 0.3V of diode CR32, as described above). When the non-inverting input 3 of the amplifier U21A falls below the 3.3V voltage level of the inverting input 2 of the amplifier U21A, the comparator behavior of the amplifier U21A causes the output 1 to swing to GND (e.g., LOW). This will turn the transistor Q41 to an OFF state, and the resistor R117 can charge the capacitor C112.

Although the capacitor C110 is charged exponentially by the resistor R116, the time for the capacitor C110 to reach the 3.3V level needed for the output 1 timeout of the amplifier U21A can be approximated by presuming a relatively constant (or approximately linear) charge current of $$\frac{12 \text{ V} - 1.5 \text{ V}}{50 \text{ k}\Omega} = 210 \text{ }\mu\text{A};$$

(with R116 rounded from 49.9 kΩ, to 50 kΩ).

Furthermore, since $C\Delta V = I\Delta T$, therefore $$\Delta T = \frac{C\Delta V}{I} = \frac{0.1 \text{ }\mu\text{F} * (3.3 \text{ V} - 0.3 \text{ V})}{210 \text{ }\mu\text{A}} = 1.4 \text{ ms}.$$

Thus, it would take about 1.4 ms for the output 1 of the amplifier U21A to swing up to HI and turn the transistor Q41 ON, which then turns OFF the LED emitter DS46. In some cases, decreasing the resistance of the resistor R116 may allow for the time to decrease to 1.0 ms, or even lower.

When the transistor Q41 switches to the OFF state, charging the capacitor C112 via the resistor R117 may begin. Similar to above, the capacitor C112 is an exponential charge (e.g., with a time constant of 43.2 kΩ*0.01 μF=432 μs), (μF=microfarads and kΩ=kiloohms) and the capacitor C112 will, in turn, charge until the Schottky diode CR33 is forward biased. In certain aspects, the forward biasing of the Schottky diode CR33 will occur nominally when the non-inverting input 5 of the amplifier U22B reaches a voltage 3.6V. For example, the non-inverting input 5 of the amplifier U22B may reach 3.6V after about 154 μs, given the time constant above, the 3.6V level, and the supply voltage V12X of 12V. Thus, this may be the time for the ramp-up of the LED emitter current to be at the plateau level, and, in some cases, a relatively high precision on values for C112 and R117 could be helpful for achieving a charge time of almost exactly 154 μs. In some cases, if the capacitor C112 is ceramic, it may include a class 1 (e.g., COG) dielectric and a have a relatively high voltage rating (e.g., 100V or higher).

The 3.6V may be determined to be the forward biasing voltage for the Schottky diode CR33 by adding the 3.3V of the V3P3 supply voltage to the Vf of the Schottky diode CR33, 0.3V. In this case, the V3P3 supply absorbs the $$\frac{12 \text{ V}}{43.2 \text{ k}\Omega} = .27 \text{ mA charge current (mA = milliampre)}$$

and a dummy load can be added to help absorb more current.

The action of the amplifier U22B causes the voltage at the non-inverting input 5 to be reflected across the plateau resistor R119 (e.g., to set a current). The transistor Q42 is controlled by the output 7 of the amplifier U22B at its gate, to effect the voltage regulation at R119, and thus current regulation through LED emitter DS46. Thus, the amplifier U22B is connected in essentially a voltage-follower configuration, where there may be little or no voltage gain, and therefore is relatively stable (e.g., unity-gain stable).

As shown, the resistor R119 may have a value of 5Ω (Ohms), and thus be configured to withstand/yield 1.0 A (Amps) of LED emitter peak pulse current. In some cases, the resistor R119 can be increased to 10Ω (e.g., for 500 mA LED emitter peak pulse current), or even as high as 50Ω (e.g., for 100 mA emitter peak pulse current). For example, the resistor R119 can be increased if there is adequate gain in the rest of the sensor signal path. In certain aspects, because the duty cycle is so small, even 5-10 W (Watts) power output during the on period of the duty cycle may result in only 50 mW (milliWatts) (average power) output from the transistor Q42 and/or the resistor R119, which would be well below each of their respective ratings.

Regarding the detector (or receiver) side circuitry 806 of FIG. 8B, a photodiode DS47 may be configured to receive the LED emitter DS46 output to convert the light emitted from the LED emitter DS46 to a voltage. This voltage may be received by an amplifier U22B (e.g., a transimpedance amplifier) with a locally-filtered offset reference of resistor R120 and capacitor C114. The resistor capacitor (RC) setup may keep the amplifier U22B away from the ground rail for a generally faster response and improved fidelity on the leading-edge. The detector side circuitry 806 further includes a capacitor C116 to preserve bandwidth (e.g., for stabilizing and/or compensating input signals). In some cases, the capacitance of the capacitor C116 can be increased. In certain aspects, a resistance of the resistor R121 can be varied to vary the voltage output from the photodiode DS47 by adjusting the gain of the amplifier U22B. As shown, scaling circuitry 808 may provide for a 12V-to-3V scale may be coupled to the P1_RX node.

Figure 9:
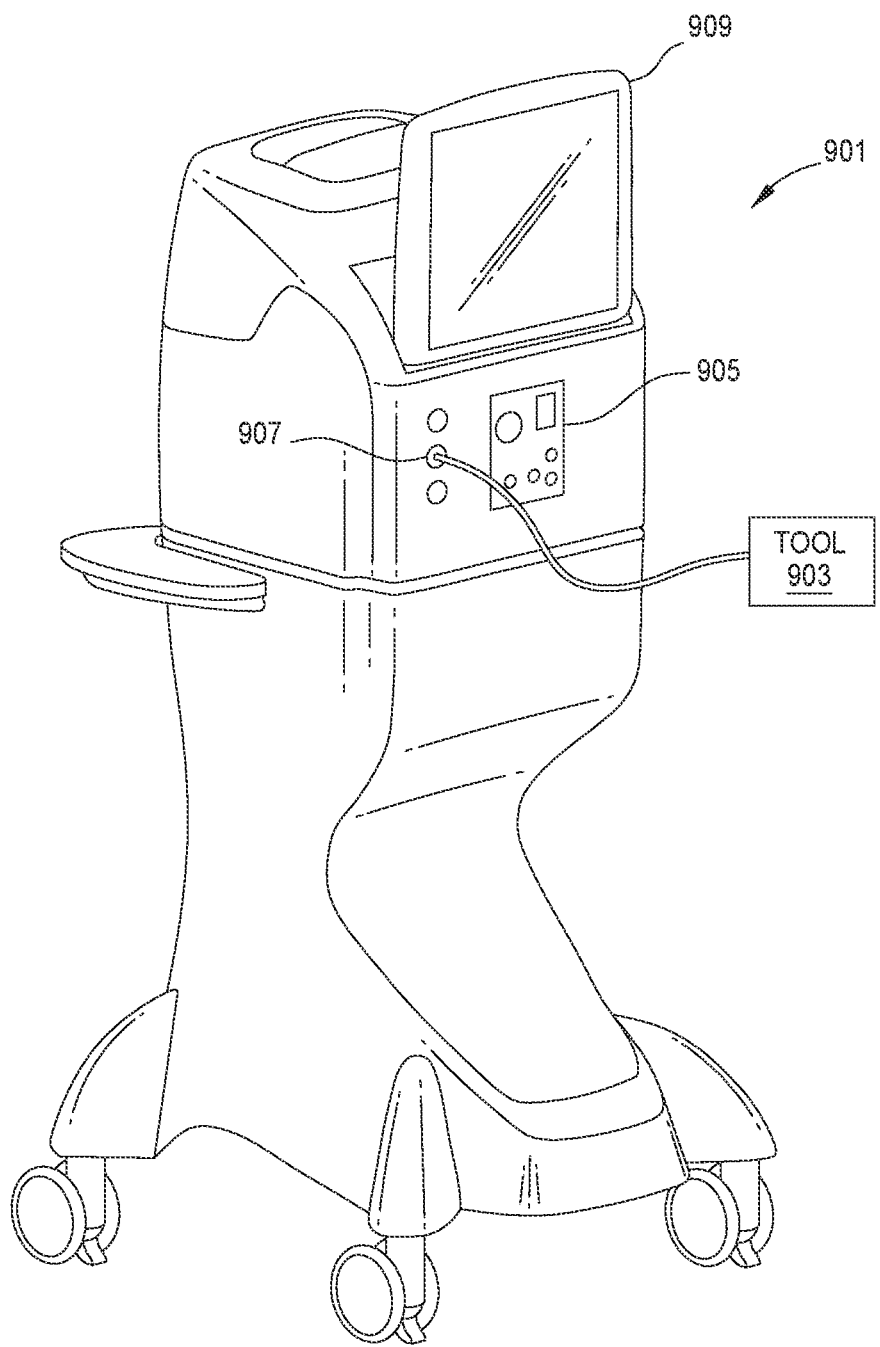
FIG. 9 illustrates a surgical console for a pneumatically powered ophthalmic surgical machine, in accordance with certain embodiments.

FIG. 9 illustrates an embodiment of a surgical console 901 for a pneumatically powered ophthalmic surgical machine in which one or more techniques described herein may be implemented. For example, the circuit 800 of FIGS. 8A and 8B may be implemented within the surgical console 901 to perform port detection. The surgical console 901 may be configured to drive one or more tools 903 (e.g., pneumatic tools). The tools 903 may include, for example, scissors, vitrectors, forceps, and injection or extraction modules. Other tools 903 may also be used. In operation, the pneumatically powered ophthalmic surgery machine of FIG. 9 may operate to assist a surgeon in performing various ophthalmic surgical procedures, such as a vitrectomy. A compressed gas, such as nitrogen, may provide the power through the surgical console 901 to power the tools 903. The surgical console 901 may include a display 909 for displaying information to a user (the display may also incorporate a touchscreen for receiving user input). The surgical console 901 may also include a fluidics module 905 (e.g., to support irrigation/aspiration functions) and a port 907 for coupling to tool 903 (e.g., coupling through pneumatic lines or tubes attached to the tools 903). The surgical console 901 may be configured to determine a characteristic of an optical pathway of the port 907 (e.g., of the fluidics module 905), according to aspects described herein. That is, circuitry (e.g., the system 100 of FIG. 1 and/or the circuit 800 of FIGS. 8A and 8B) may be included in the surgical console 901 to detect the health of an optical pathway within the port 907 during operation to ensure the pathway is clear.

Figure 10A:
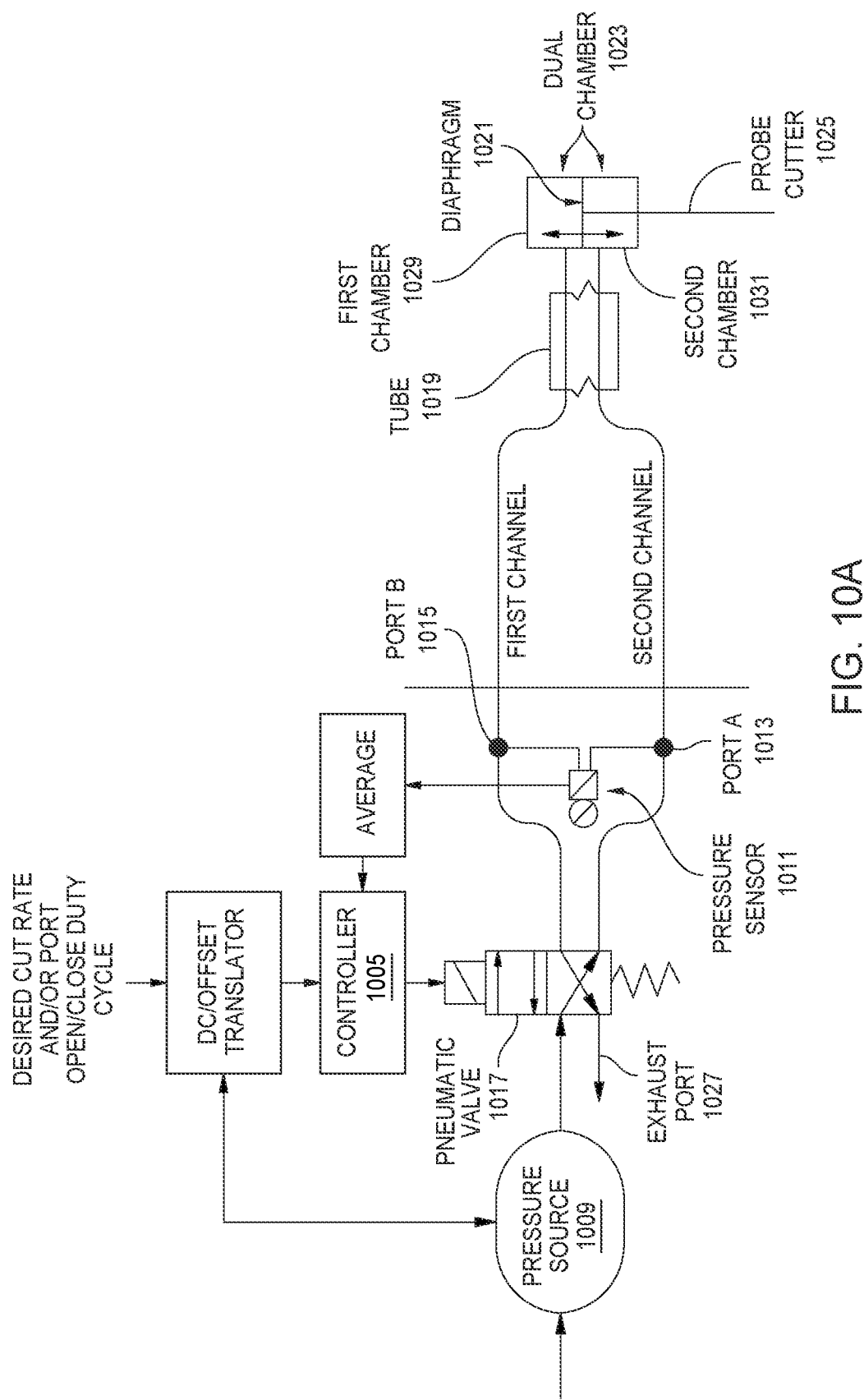
FIGS. 10A and 10B illustrate a schematic of a pneumatic system for a pneumatically powered vitrectomy machine, in accordance with certain embodiments.
Figure 10B:
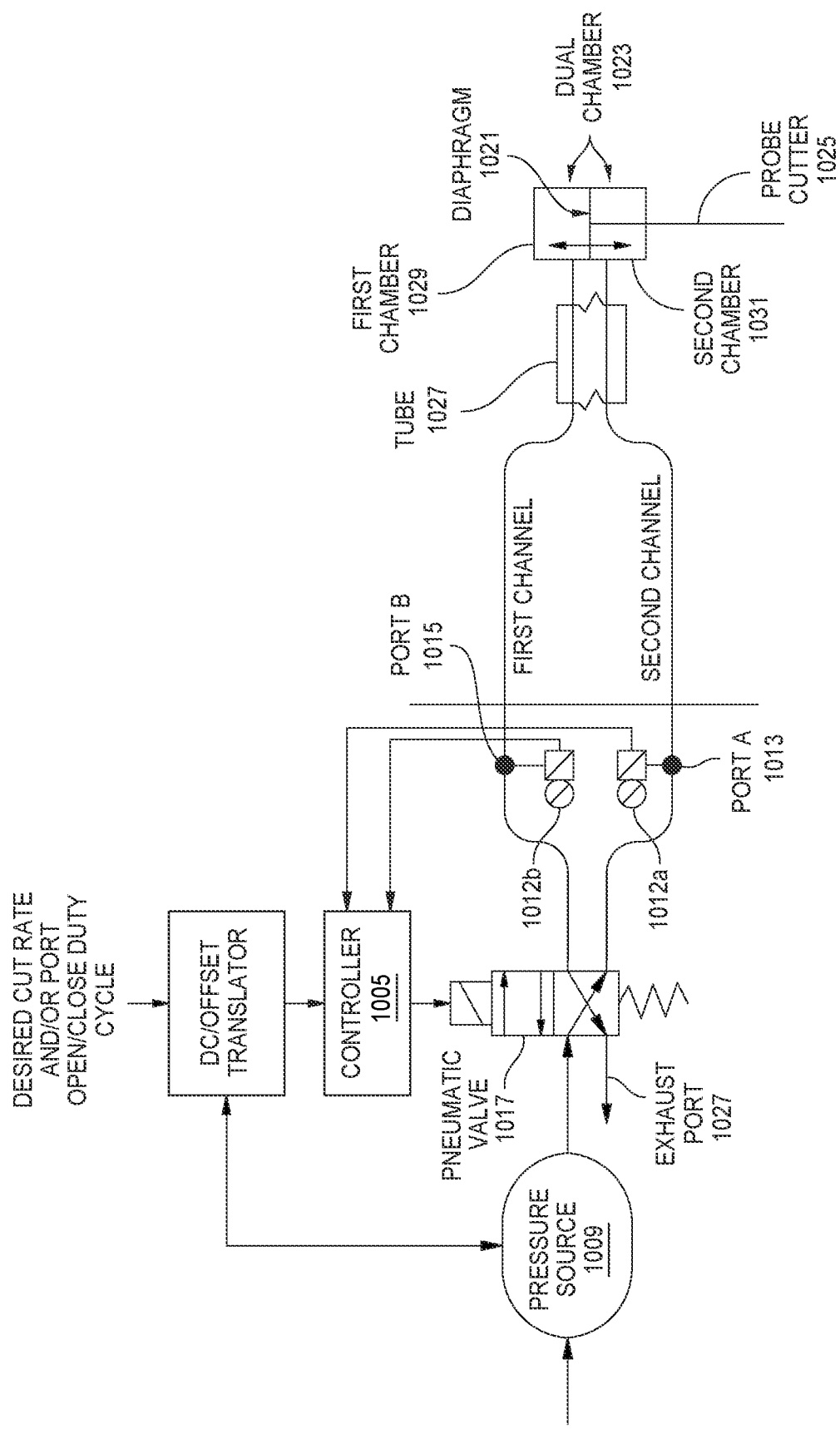

FIGS. 10A and 10B illustrate a schematic of a pneumatic system for a pneumatically powered vitrectomy machine. As seen in FIGS. 10A and 10B, the pneumatic system may include a pneumatic valve 1017 coupling a pressure source 1009 (e.g., a regulated pressure source such as a gas cylinder or a wall outlet gas supply) to output port A 1013 ("port A") and output port B 1015 ("port B"). The port A and port B may be coupled to the tool 903 through the port 907. Furthermore, a system (e.g., the system 100 of FIG. 1) may be placed in the port(s) A and/or B to perform port detection (described above) for the port 907. In some embodiments, the pneumatic valve 1017 may be controlled by controller 1005 (e.g., corresponding to the controller 114 of FIG. 1). In some embodiments, the pressure of the pressure source 1009 may also be regulated by controller 1005 or a separate controller (e.g., internal to the surgical console 901). The controller 1005 may regulate pressure (e.g., to balance between lower pressures for reducing gas consumption and higher pressures for faster cut rates and/or to increase a dynamic range of available cut rates). In certain aspects, the controller 1005 may include circuitry and/or be configured to determine a characteristic of an optical pathway, as described herein.

In some embodiments, the components of the pneumatic system may be incorporated in one or more manifolds (e.g., machined out of a metal, such as aluminum) or manifold plates. The manifolds may be gas tight, and include various fittings and couplings, and be capable of withstanding relatively high gas pressures. The manifolds may be manufactured as individual pieces or they may be manufactured as a single piece. In various embodiments, the components of the pneumatic system (e.g., in the manifold) may be incorporated inside the surgical console 901.

The pneumatic valve 1017 may include a solenoid that operates to move the pneumatic valve 1017 to one of the two positions (e.g., see FIGS. 10A and 10B) as directed by control signals from controller 1005. In a first position, pneumatic valve 1017 may allow pressurized gas to pass through pneumatic valve 1017 to output port B 1015 to provide pneumatic power to the probe cutter 1025 while venting pressurized gas from port A through an exhaust port 1027. In a second position, the pneumatic valve 1017 may provide pressurized gas to port A and vent pressurized gas from output port B 1015 through the exhaust port 1027. In this position, pressurized gas may pass through port A to provide pneumatic power to a tool 703 (e.g., probe cutter 1025). Thus, when the pneumatic valve 1017 is in the first position, the first chamber 1029 of the dual chambers 1023 may be charged while the second chamber 1031 may be discharged. When the pneumatic valve 1017 is in the second position the second chamber 1031 may be charged while the first chamber 1029 may be discharged. In certain embodiments, the probe cutter 1025 may be moved by a diaphragm 1021 that in turn oscillates as pressurized gas is alternately directed to ports A and B and into respective chambers of the dual chamber 1023. As shown in FIGS. 10A and 10B, probe cutter 1025 may be attached to ports A and B through tube 1019. However, in other embodiments, separate tubes for each port may also be used. Note that in the pneumatic system shown in FIG. 10A only a single pressure sensor 1011 is used while in the pneumatic system shown in FIG. 10B two pressure sensors 1012a and 1012b are used. Also, although an isolation valve is not shown in FIGS. 10A and 10B, in certain aspects, an isolation valve may be coupled to pneumatic valve 1017 to provide pressurized gas to pneumatic valve 1017 or stop the flow of pressurized gas to pneumatic valve 1017.

Figure 11:
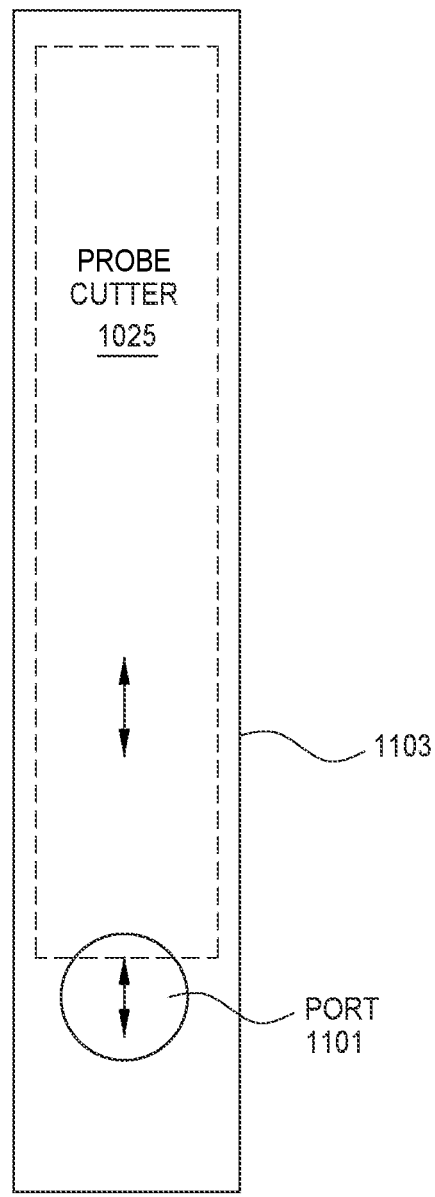
FIG. 11 illustrates the cutting device of a surgical probe, in accordance with certain embodiments.

As seen in FIG. 11, the probe cutter 1025 may act as a cutting device. The probe cutter 1025 may reciprocate inside an outer tube 1103 with a cutter port 1101. As the probe cutter 1025 moves back and forth, the probe cutter 1025 may alternately open and close cutter port 1101 with a sharpened tip of the probe cutter 1025. Each cycle of the probe cutter 1025 through outer tube 1103 may cut through material such as vitreous in the cutter port 1101 as the probe cutter 1025 is closing.

Example Aspects

Aspect 1: A method for determining a characteristic of an optical pathway corresponding to a fluid pathway of a medical device, comprising increasing, over a time period that starts at a first time, a current input to a light emitting element (LEE); receiving, by a light detection element, an output of the LEE via the optical pathway during the time period; converting, during the time period, the LEE output to a voltage output; determining a second time in the time period when the voltage output crosses a threshold; and determining the characteristic of the optical pathway between the LEE and the light detection element based on a difference between the second time and the first time.

Aspect 2: The method of Aspect 1, wherein the characteristic of the optical pathway comprises at least one of an amount of blockage or an amount of decay within the optical pathway.

Aspect 3: The method of Aspect 1 or 2, wherein the threshold comprises a saturation voltage of an amplifier coupled to the light detection element.

Aspect 4: The method of any of Aspects 1-3, wherein determining the characteristic of the optical pathway between the LEE and the light detection element based on the difference between the second time and the first time comprises determining whether the difference is greater than a time value.

Aspect 5: The method of Aspect 4, further comprising, when the difference is greater than the time value, providing an indication of at least one of blockage or decay of the optical pathway.

Aspect 6: The method of any of Aspects 1-5, wherein the optical pathway is disposed within a pneumatic port.

Aspect 7: The method of any of Aspects 1-6, wherein the current input to the LEE is increased by using a resistor capacitor (RC) circuit having a time constant associated with the time period.

Aspect 8: A method for determining a characteristic of an optical pathway corresponding to a fluid pathway of a medical device, comprising emitting a light output from an LEE over a time period that starts at a first time; receiving, by a light detection element via the optical pathway, the LEE output during the time period; converting, during the time period, the LEE output to a voltage output; varying a gain of an amplifier coupled to the voltage output during the time period to vary the voltage output; determining a second time in the time period when the voltage output crosses a threshold; and determining the characteristic of the optical pathway between the LEE and the light detection element based on a difference between the second time and the first time.

Aspect 9: The method of Aspect 8, wherein the characteristic of the optical pathway comprises at least one of an amount of blockage or an amount of decay within the optical pathway.

Aspect 10: The method of Aspect 8 or 9, wherein varying the gain of the amplifier comprises varying a resistance coupled to the amplifier.

Aspect 11: The method of any of Aspects 8-10, wherein the threshold comprises a saturation voltage of the amplifier.

Aspect 12: A method for determining a characteristic of an optical pathway corresponding to a fluid pathway of a medical device, comprising applying a first current input to an LEE; receiving, by a light detection element, an output of the LEE via the optical pathway while the first current input is applied to the LEE; converting the LEE output to a voltage output; determining whether the voltage output is greater than a first threshold; when the voltage output is greater than the first threshold, applying a second current input to the LEE; receiving, by the light detection element, the output of the LEE via the optical pathway while the second current input is applied to the LEE; converting the LEE output to another voltage output; determining whether the other voltage output is greater than a second threshold, wherein the second current is less than first current, and the second threshold is less than the first threshold; and determining the characteristic of the optical pathway based on whether the other voltage output is greater than the second threshold.

Aspect 13: The method of Aspect 12, wherein the characteristic of the optical pathway comprises at least one of an amount of blockage or an amount of decay within the optical pathway.

Aspect 14: The method of Aspect 12 or 13, wherein the first voltage output comprises a saturation voltage of an amplifier coupled to the light detection element.

Aspect 15: The method of any of Aspects 12-14, further comprising, when the other output voltage is less than the second threshold, providing an indication of at least one of blockage or decay of the optical pathway.

Aspect 16: The method of any of Aspects 12-15, wherein the optical pathway is disposed within a pneumatic port.

Aspect 17: A method for determining a characteristic of an optical pathway corresponding to a fluid pathway of a medical device, comprising applying a current input to an LEE; receiving, by a light detection element, an output of the LEE via the optical pathway while the first current input is applied to the LEE; converting the LEE output to a voltage output; determining whether the voltage output is greater than a first threshold; when the voltage output is greater than the first threshold, applying a second current input to the LEE; receiving, by the light detection element, the output of the LEE via the optical pathway while the second current input is applied to the LEE; converting the LEE output to another voltage output; determining whether the other voltage output is greater than a second threshold, wherein the second current is less than first current; and the second threshold is less than the first threshold; and determining the characteristic of the optical pathway based on whether the other voltage output is greater than the second threshold.

Aspect 18: The method of Aspect 17, wherein the characteristic of the optical pathway comprises at least one of an amount of blockage or an amount of decay within the optical pathway.

Aspect 19: The method of Aspect 17 or 18, wherein varying the gain of the amplifier comprises varying a resistance coupled to the amplifier.

Aspect 20: The method of any of Aspects 17-19, wherein the first threshold is a saturation voltage of the amplifier.

Aspect 21: The method of any of Aspects 17-20, further comprising, when the other output voltage is less than the second threshold, providing an indication of at least one of blockage or decay of the optical pathway.

Aspect 22: The method of any of Aspects 17-21, wherein the optical pathway is disposed within a pneumatic port.

Aspect 23: An apparatus for determining a characteristic of an optical pathway corresponding to a fluid pathway of a medical device, comprising means to perform one or more of the methods of Aspects 1-22.

Aspect 24: An apparatus for determining a characteristic of an optical pathway corresponding to a fluid pathway of a medical device, comprising transmitter circuitry coupled to a light emitting element and receiver circuitry coupled to a light detection element, configured to perform one or more of the methods of Aspects 1-22.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A method for determining a characteristic of an optical pathway corresponding to a fluid pathway of a medical device, comprising:
   increasing, over a time period that starts at a first time, a current input to a light emitting element (LEE);
   receiving, by a light detection element, an output of the LEE via the optical pathway during the time period;
   converting, during the time period, the output of the LEE to a voltage output;
   determining a second time in the time period when the voltage output crosses a threshold; and
   determining the characteristic of the optical pathway between the LEE and the light detection element based on a difference between the second time and the first time.

2. The method of claim 1, wherein the characteristic of the optical pathway comprises at least one of an amount of blockage or an amount of decay within the optical pathway.

3. The method of claim 1, wherein the threshold comprises a saturation voltage of an amplifier coupled to the light detection element.

4. The method of claim 1, wherein determining the characteristic of the optical pathway between the LEE and the light detection element based on the difference between the second time and the first time comprises determining whether the difference is greater than a time value.

5. The method of claim 4, further comprising, when the difference is greater than the time value, providing an indication of at least one of blockage or decay of the optical pathway.

6. The method of claim 1, wherein the optical pathway is disposed within a pneumatic port.

7. The method of claim 1, wherein the current input to the LEE is increased by using a resistor capacitor (RC) circuit having a time constant associated with the time period.

* * * * *